(12) United States Patent
Shirai et al.

(10) Patent No.: US 7,369,692 B2
(45) Date of Patent: May 6, 2008

(54) SKIN OBSERVING APPARATUS

(75) Inventors: Yasuo Shirai, Saitama (JP); Hiroshi Misawa, Saitama (JP); Tsuyoshi Kawai, Saitama (JP)

(73) Assignee: Moritex Corporation, Tokyo (JP)

( * ) Notice: Subject to any disclaimer, the term of this patent is extended or adjusted under 35 U.S.C. 154(b) by 751 days.

(21) Appl. No.: 10/865,902

(22) Filed: Jun. 14, 2004

(65) Prior Publication Data
US 2004/0257439 A1  Dec. 23, 2004

(30) Foreign Application Priority Data
Jun. 17, 2003 (JP) .............................. 2003-171665

(51) Int. Cl.
G06K 9/00 (2006.01)
H04N 7/18 (2006.01)

(52) U.S. Cl. .................... 382/128; 382/108; 348/77
(58) Field of Classification Search .................... None
See application file for complete search history.

(56) References Cited

U.S. PATENT DOCUMENTS 6,118,476 A      9/2000 Morito et al.
7,006,223 B2 *   2/2006 Mullani .................. 356/369

2003/0012461 A1  1/2003 Satoh et al.
2003/0026110 A1  2/2003 Satoh et al.

FOREIGN PATENT DOCUMENTS

JP            3007978            12/1999

* cited by examiner

Primary Examiner—Bhavesh M. Mehta
Assistant Examiner—Charles Kim
(74) Attorney, Agent, or Firm—Greenblum & Bernstein, P.L.C.

(57) ABSTRACT

A skin observing apparatus capable of observing the skin texture, blotches caused from subcutaneous pigmentation and skin roughness caused from keratin abrasion by a single unit of image pick-up device without using a polarization plate for observing blotches or consumption articles such as a keratin sampling seal, the apparatus including an image pick-up head having an view hole to be in contact with a skin and, provided inside the image pick-up device, an image pick-up device for picking-up images of the skin through the view hole, and an illumination system comprising three systems, that is, a texture observing illumination system for irradiating a white light to the view hole along the image pick-up light axis (X), a keratin abrasion observing illumination system for irradiating a white light to the view hole from the lateral direction thereof, and a subcutaneous pigment observing illumination system for irradiating a UV-light to the view hole.

2 Claims, 2 Drawing Sheets

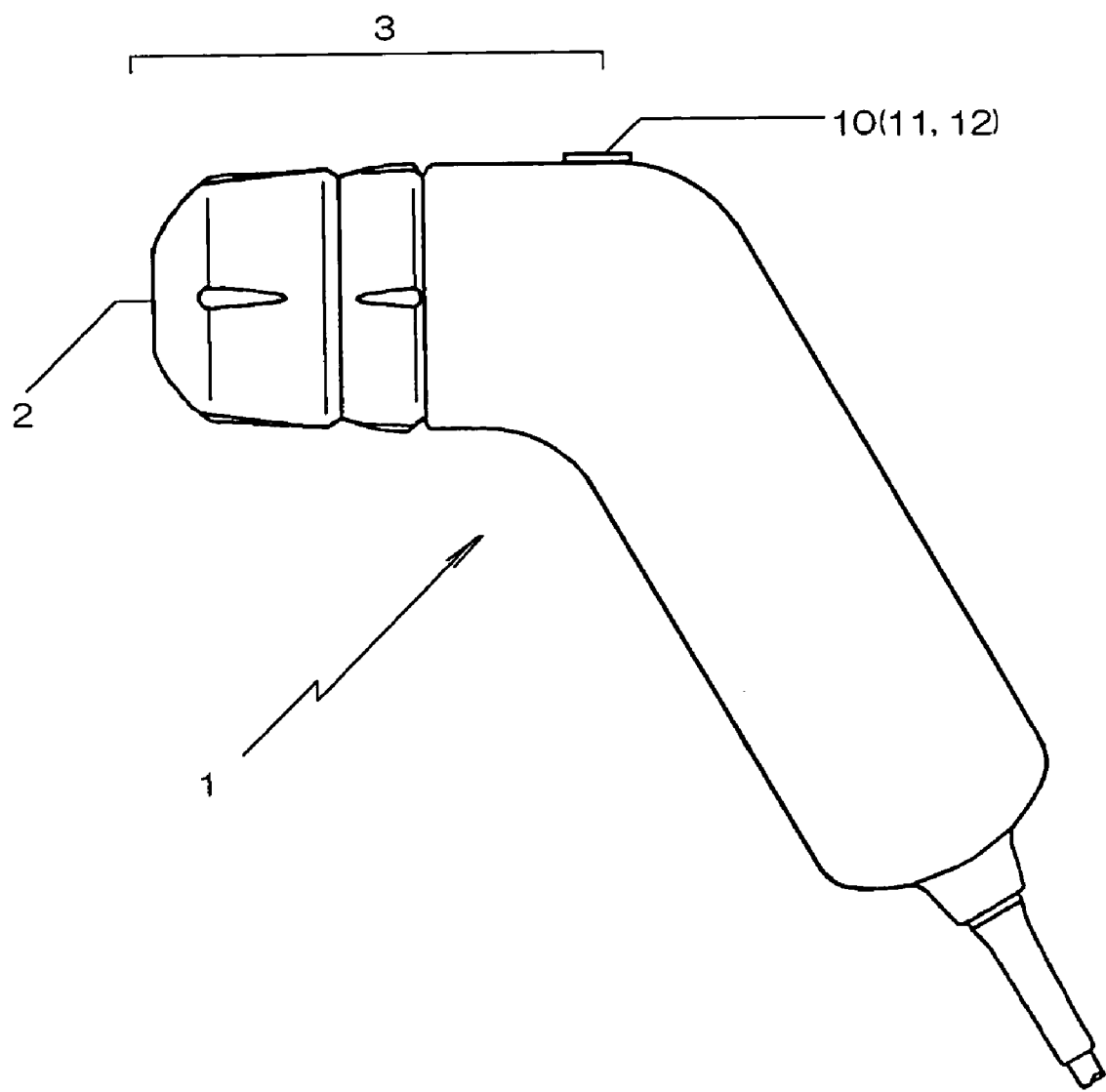

SKIN OBSERVING APPARATUS

BACKGROUND OF THE INVENTION

1. Field of the Invention

Figure 1:
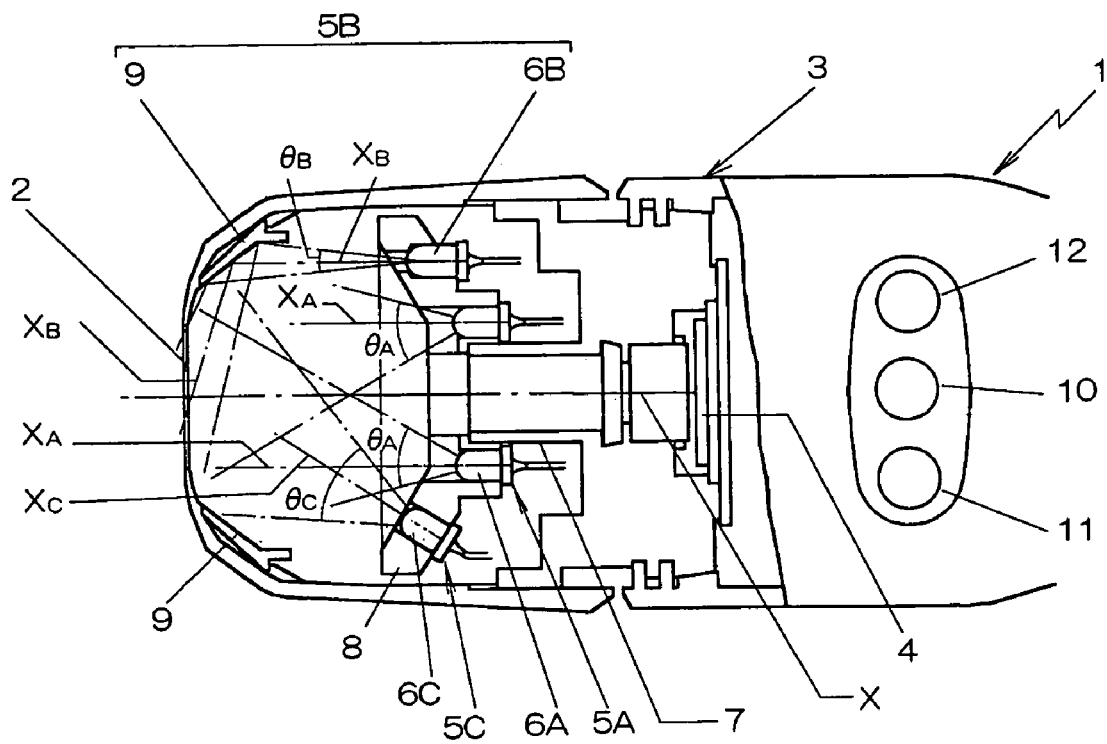

The present invention concerns a skin observing apparatus including an image pick-up head having a view hole formed at the top end thereof, and an image pick-up device for picking-up images of a skin through the view hole in a state of bringing the top end thereof into contact with the skin, and an illumination system for irradiating an illumination light to the skin, the image pick-up device and the illumination system being provided inside the image pick-up head.

2. Statement of the Related Art

Recently, various measuring instruments and diagnostic instruments have been introduced for sales promotion of cosmetics not only in the sales floors of department stores but also in cosmetics stores in shopping areas.

Among them, illumination-incorporated observing apparatus have become important tools for sales promotion since the apparatus can magnify skins at a high magnification ratio, display textures formed of fine twilled ridges running lengthwise, crosswise and slantwise, blotches caused by subcutaneous pigmentation, etc. on a monitor and enable explanation for the situations of skins to customers while presenting video images.

By the way, in a case of observing the texture by an illumination-incorporated type image pick-up apparatus, illumination light irradiated to the surface of a skin and reflected directly therefrom is mainly picked-up.

Further, in a case of observing blotches, a polarization plate located on the side of a light source and another polarization plate located on the side of the image pick-up device are situated in a cross nicol state, and an indirect reflection light from the inside of the skin is mainly picked-up while cutting the direct reflection light from the skin surface, so that blotches can be picked-up distinctly.

Accordingly, the texture as the surface condition of the skin and blotches caused by subcutaneous pigment can be observed respectively by selectively switching an illumination system providing direct reflection and an illumination system providing indirect reflection, or by changing the direction of the polarization plates disposed in one identical illumination system (refer to Japanese Patent No. 3007978).

However, in a case of observing blotches, at least two polarization plates have to be used and one of them has to be situated always on the axis of the image pick-up light of the image pick-up device.

Accordingly, even in a case of not requiring the use of the polarization plate, a light incident to the image pick-up device transmits through at least one polarization plate to result in a problem that the amount of the illumination light can not be utilized effectively.

While such a problem can be avoided by advancing or retracting the polarization plate to and from the axis of the image pick-up light, this needs a complicate advancing/retracting mechanism for the polarization plate, to leave a problem that the size of the apparatus is inevitably enlarged.

Further, in a case of observing the abraded state of keratin as an index of skin roughness, a disposable keratin sampling seal coated with an adhesive has been adhered on the surface of a skin to sample keratin and the amount of the sampled keratin has been judged by optical measurement.

However, the amount of sampling differs depending on the way of adhering the keratin sampling seal, strength of adhesion, releasing speed and way of releasing conducted by cosmetic make-up stuffs.

Further, in a case of confirming the effect of cosmetics, the effect of the cosmetics can not be confirmed by sampling keratin after the use of the cosmetics from an area identical with the area from which the keratin was sampled before use. Accordingly, it is necessary to sample keratin from another area. However, since it can not be assured whether the two areas suffer from identical extent of skin roughness, comparison of data between them has no meaning to leave a problem that the effect can not be confirmed.

Further, since the keratin sampling seal is a consumption article, if it happens to be out of stock, measurement is not possible.

SUMMARY OF THE INVENTION

In view of the above, the present invention intends to make it possible for observing skin textures, blotches caused from subcutaneous pigmentation, skin roughness caused from keratin abrasion, by a single unit of an image pick-up apparatus by using neither a polarization plate for blotch observation nor consumption articles such as a keratin sampling seal.

The foregoing subject can be attained in accordance with the present invention by a skin observing apparatus including an image pick-up head having a view hole formed at the top end thereof, and an image pick-up device for picking-up images of a skin through the view hole in a state of bringing the top end thereof into contact with the skin, and an illumination system for irradiating an illumination light to the skin, the image pick-up device and the illumination system being provided inside the image pick-up head, wherein the illumination system comprises three illumination system, that is, a texture observing illumination system of irradiating a white light to the view hole along the axis of an image pick-up light, a keratin abrasion observing illumination system for irradiating a white light to the view hole from the lateral side thereof, and a subcutaneous pigment observing illumination system for irradiating a UV-light to the view hole.

According to the present invention, when the image pick-up head is brought into contact with a skin and the skin is irradiated by one of the texture observing illumination system, the keratin abrasion observing illumination system and the subcutaneous pigment observing illumination system, the images of the skin can be picked-up through the view hole by the image pick-up device.

When a white light is irradiated as the illumination light by the texture observing illumination system to the view hole substantially parallel with the axis of the image pick-up light, since the illumination light is irradiated through the view hole to the skin, directly reflected on the skin surface and entered into the image pick-up device, images for the texture as the condition of the skin surface can be picked-up distinctly.

Particularly, since the axis of the illumination light is substantially parallel with the axis of the image pick-up light, images of twilled ridges running lengthwise, crosswise and slantwise on the skin surface can be picked-up distinctly without forming shades due to the unevenness of the twilled ridges.

Further, when a white light is irradiated as the illumination light by the keratin abrasion observing illumination system to the view hole from the lateral direction thereof, since the illumination light is irradiated through the view hole substantially parallel with the skin surface, images for protuberances on the skin are picked-up in a whity state undergoing the illumination light from the lateral direction while the valleys are shaded from the illumination light and images are picked-up somberly.

Accordingly, since the portions riding up or tending to be peeled by keratin abrasion are raised from the periphery thereof, images for the portions can be picked-up distinctly in a whity state.

Further, when a UV-light is irradiated as the illumination light by the subcutaneous pigment observing illumination system to the view hole, since the UV-light has a short wavelength, the light is transmitted through the skin and reflected at the subcutaneous area suffering from pigmentation and then entered to the image pick-up device, images for blotches or freckles caused by subcutaneous pigments can be picked-up distinctly by picking-up images of subcutaneous pigments.

DESCRIPTION OF THE ACCOMPANYING DRAWINGS

Figure 2:
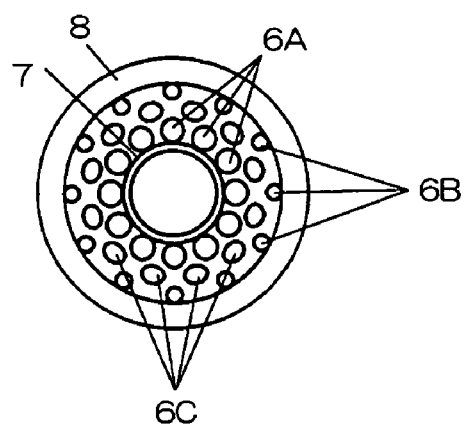

A referred embodiment of the present invention will be described in details based on the drawings, wherein FIG. 1 is a cross sectional view showing a main portion of a skin observing apparatus according to the present invention;

FIG. 2 is an explanatory view showing the arrangement of light emitting elements; and FIG. 3 is a view for the entire appearance.

DESCRIPTION OF PREFERRED EMBODIMENTS

The present invention is to be described specifically by way of a preferred embodiment with reference to the drawings.

A skin observing apparatus 1 shown in FIG. 1 to FIG. 3 includes a dome-shaped image pick-up head 3 having a view hole 2 formed at the top end thereof, in which an image pick-up device 4 for picking-up images of skins through the view hole 2 in a state of bringing the top end of the head into output with a skin and an illumination system for irradiating an illumination light to the skin are provided. When the apparatus is connected with a computer or like other equipment having a video signal processing function (not illustrated), images picked-up by the image pick-up device 4 can be displayed on a display unit (not illustrated).

The illumination system comprises a texture observing illumination system 5A for irradiating a white light to the view hole 2 along the direction of an image pick-up optical axis X, a keratin abrasion observing illumination system 5B for irradiating a white light to the view hole 2 from the lateral direction thereof, and a subcutaneous pigment observing illumination system 5C for irradiating a UV-light UV-A (at a wavelength of about 390 nm) to the view hole 2.

Then, the texture observing illumination system 5A comprises high luminance white LED (white light emitting elements) 6A arranged circularly at the periphery of the image pick-up light axis X. LED 6A are mounted each to a circular substrate 8 externally disposed to a lens cylinder 7 for the image pick-up device 4 such that the illumination light axis $X_A$ is substantially parallel with the image pick-up light axis X, and emission angle $\theta_A$ is selected in accordance with the diameter of the view hole 2 such that the illumination light covers substantially the entire area of the view hole 2.

Further, the keratin abrasion observing illumination system 5B comprises high luminance white LED (white light emitting element) 6B arranged circularly to the outside of the LED 6A of the texture observing illumination system 5A and a circular reflection mirror 9 for reflecting the illumination light and irradiating the same from the lateral direction to the view hole 2.

LED 6B are attached each to the circular substrate 8 such that the illumination light axis $X_B$ thereof is substantially parallel with the image pick-up light axis, and the illumination light axis $X_B$ thereof is bent by the circular reflection mirror 9.

The emission angle $\theta_B$ for the LED 6B is selected smaller in accordance with the width of the reflection mirror 9 such that the illumination light is not irradiated directly to the view hole 2 but almost of the light is irradiated to the reflection mirror 9.

With the constitution described above, when observing a skin by the keratin abrasion observing illumination system 5B, since all the emission light from the LED 6B are reflected on the reflection mirror 9 and then irradiated to the skin as the emission light in the lateral direction, the keratin abrasion state can be observed distinctly.

Further, the subcutaneous pigment observing illumination system 5C comprises UV-light LED (UV-light emitting elements) 6C arranged circularly to the outside of the LED 6A of the texture observing illumination system 5A.

The UV-light LED 6C are attached each to the circular substrate 8 each being inclined such that the illumination light axes $X_C$ are collected to the center of the view hole 2, and the emission angle $\theta_C$ thereof is selected in accordance with the diameter of the view hole 2 such that the illumination light covers the entire area of the view hole 2.

Then, a main body of the skin observing apparatus 1 has a main ON-OFF switch 10, an illumination changing switch 11 for selectively actuating each of the illumination systems 5A to 5C to emit light, and a shutter switch 12 for recording images displayed by the image pick-up device 4.

An example of the constitution according to the present invention is as has been described above and the operation thereof is to be described.

The skin observing apparatus 1 is used, for example, in a case of picking-up images for the skins of a customer who intends to purchase cosmetics, explaining the situation of the skins while presenting video images to the customer and, after applying make-up with selected cosmetics, picking-up skin images again and explaining the customer how the skin condition has been improved while presenting the improved images to the customer.

The image pick-up head 3 is brought into contact with an optional area to be checked of a face before make up, and the texture, keratin abrasion and blotches are observed at an identical area or respective optional areas while switching the illumination lights from the illumination systems 5A to 5C successively.

At first, in a case of observing the texture, when the main switch 10 is turned-on, the texture observing illumination system 5A is lit, a white light is irradiated along the illumination light axis $X_A$ substantially parallel with the image pick-up light axis X through the view hole 2 to a skin, and the illumination light is directly reflected on the surface of the skin and entered to the image pick-up device 4.

As described above, since the illumination light axis $X_A$ is substantially parallel with the image pick-up light axis X, shades due to unevenness of fine twilled ridges running lengthwise, crosswise and slantwise on the skin surface are not formed and images for ridge lines thereof can be picked-up distinctly and the texture showing the situation of the skin surface is displayed clearly.

Further, since the skin images can be picked-up only by irradiation of the white light from the high luminance white diodes 6A with-no effect of the ambient light, the skin images can be always picked-up under the identical condition and the skin color can be observed exactly.

Then, when the shutter switch 12 is pushed, static picture images picked-up from the texture are intaken and stored in a predetermined memory area of a computer.

Then, in a case of observing the keratin abrasion state causing skin roughness, when the illumination changing switch 11 is pushed, the texture observing illumination system 5A is extinguished and the keratin abrasion observing illumination system 5B is lit, in which the white light irradiated from the LED 6B at a narrow emission angle $\theta_B$ is reflected on the reflection mirror 9 and irradiated to the view hole 2 from the lateral direction at an angle substantially parallel with the skin surface.

Thus, images for protuberances of the skin are picked-up in a whity state undergoing the illumination light from the lateral direction, while the images for valleys of the skin are picked-up somberly being shaded from the illumination light.

Since the keratin abrasion occurs from the edge of the valleys of the twilled ridges forming the texture, riding-up portions or portions tending to be abraded are raised from the periphery and picked-up in a whity state, while the valleys at the periphery thereof are shaded and picked-up somberly and the abrasion state can be observed distinctly by the contrast between them.

Then, when the shutter switch 12 is pushed, static picture images picked-up for the keratin abrasion state are intaken and stored in a predetermined memory area of the computer.

Finally, in a case of observing the situation of subcutaneous pigmentation causing blotches, when the illumination changing switch 11 is pushed, the keratin abrasion observing illumination system 5B is extinguished and the subcutaneous pigment observing illumination system 5C is lit, and UV-light is irradiated from the LED 6C through the view hole 2 to the skin.

Thus, since the UV-light is transmitted through the skin, reflected at the subcutaneous region suffering from pigment deposition and entered to the image pick-up device 4, subcutaneous pigment and blotches and freckles caused thereby can be observed distinctly.

When the shutter switch 12 is pressed, static picture images picked-up from the blotches and freckles are intaken and stored in a predetermined memory area of the computer.

Then, after applying make-up, when the images by the illumination light of the texture observing illumination system 5A, images by the illumination light of the keratin abrasion observing illumination system 5B and images by the illumination light of the subcutaneous pigment observing illumination system 5C are picked-up in the same manner as described above and compared with the images before applying make-up, the effect obtained by the make-up can be clearly explained to the customer.

As has been described above, the present invention can provide an excellent effect capable of observing the texture of a skin, blotches and freckles caused by subcutaneous pigment deposition, and the roughness of skin caused by keratin abrasion by a single unit of an image pick-up apparatus using neither a blotch observing polarization plate nor consumption articles such as a keratin sampling seal.

The present disclosure relates to subject matter contained in priority Japanese Patent Application No. 2003-171,665 filed on Jun. 17, 2003, the contents of which is herein expressly incorporated by reference in its entirety.

What is claimed is:

1. A skin observing apparatus, comprising:
an image pick-up head having a view hole formed at a top end thereof;
an image pick-up device that picks-up images of a skin through the view hole when the top end of the image pick-up head is in contact with the skin; and
an illumination system that irradiates illumination light on the skin, the image pick-up device and the illumination system being provided inside the image pick-up head,
wherein the illumination system comprises a texture observing illumination system that irradiates white light to the view hole along an axis of an image pick-up light, a keratin abrasion observing illumination system that irradiates a white light to the view hole from a lateral direction thereof, and a subcutaneous pigment observing illumination system that irradiates a UV-light to the view hole,
the texture observing illumination system comprises white light emitting elements arranged circularly at a periphery of the image pick-up light axis adjacent therewith,
the keratin abrasion observing illumination system comprises white light emitting elements arranged circularly outside of the white light emitting elements of the texture observing illumination system, and a reflection mirror that reflects illumination light of the white light emitting elements of the keratin abrasion observing illumination system and irradiates the same to the view hole from the lateral direction thereof, and
the subcutaneous pigment observing illumination system comprises UV-light emitting elements arranged circularly outside of the white light emitting elements of the texture observing illumination system.

2. A skin observing apparatus according to claim 1, wherein the light emitting elements of the texture observing illumination system, the keratin abrasion observing illumination system and the subcutaneous pigment observing illumination system are arranged on a circular substrate disposed externally to a lens cylinder of the image pick-up device.

* * * * *